United States Patent [19]

Stepanov et al.

[11] 4,100,028

[45] Jul. 11, 1978

[54] METHOD FOR PURIFICATION OF PROTEOLYTIC ENZYMES

[76] Inventors: Valentin Mikhailovich Stepanov, ulitsa Chertanovskaya, 33, korpus 1, kv. 247; Galina Nikolaevna Rudenskaya, ulitsa Tsandera, 7, kv. 281, both of Moscow, U.S.S.R.

[21] Appl. No.: 804,248

[22] Filed: Jun. 7, 1977

[30] Foreign Application Priority Data

Jun. 9, 1976 [SU] U.S.S.R. ................................ 2370306

[51] Int. Cl.$^2$ .............................................. C07G 7/026
[52] U.S. Cl. .................................................. 195/66 R
[58] Field of Search .......... 195/66 R, 63, 68, DIG. 11

[56] References Cited

U.S. PATENT DOCUMENTS

| | | | |
|---|---|---|---|
| 3,904,478 | 9/1975 | Dean et al. ............................. | 195/63 |
| 4,020,268 | 4/1977 | Nishikawa et al. ............. | 195/66 R X |
| 4,030,977 | 6/1977 | Fujii et al. .......................... | 195/66 R |

*Primary Examiner*—Lionel M. Shapiro
*Attorney, Agent, or Firm*—Lackenbach, Lilling & Siegel

[57] ABSTRACT

A biological source of proteolytic enzymes such as a culture liquid is brought into contact with a biospecific sorbent prepared by covalent addition of a naturally-occurring polypeptide, viz. bacitracin, to agarose. The sorbed enzyme is eluted with salt buffer solutions.

The method of the present invention makes it possible to recover a colorless enzyme; owing to the sorbent selectivity a substantial effect is achieved in a single-stage purification process. The method may be used for recovering proteolytic enzymes of various classes including carboxyl, serine, thiol, metal proteinases and exopeptidases. The novel biospecific sorbent enables purification of various proteolytic enzymes with a yield of from 75 to 95% and with an increased, by 2 to 500 times, activity depending on the purity of the starting material.

3 Claims, No Drawings

METHOD FOR PURIFICATION OF PROTEOLYTIC ENZYMES

The present invention relates to medical and microbiological industries and, in particular, to the preparation of enzymes and, more specifically, to methods for purification of proteolytic enzymes.

FIELD OF THE INVENTION

The present invention is useful in the preparation of various proteolytic enzymes of a high purity grade useful in medical practice for the treatment of certain diseases, in medical industry for the production of purified therapeutic and prophylactic serum; and in the food industry for the production of cheese, wine, beer. Furthermore, the present invention is suitable for the production of reagents for scientific research.

BACKGROUND OF THE INVENTION

To produce pure enzymes from naturally-occurring sources such as biological liquids, extracts of organs and tissues, cells of microorganisms, fermentation broth, it is necessary to separate the accompanying proteins including other enzymes, nucleic acids and products of decomposition thereof, low-molecular compounds and salts. Conventional methods of recovery and purification of enzymes are based on differences in physico-chemical properties of enzymes and other components of the mixture to be separated such as molecular weight, charge, and solubility. These methods are exemplified by fractional precipitation of proteins by means of salts and organic solvents; gel-filtration, ultra-filtration, on-exchange chromatography. However, each of the prior art methods is insufficiently effective. Satisfactory results are obtained by combination of several methods which, however, is associated with great losses of enzymes and increased production and labor costs. The method of biospecific or affinity chromatography principally differs from the traditional methods in that it is based on the use of the most individualized property of an enzyme, i.e. its ability of selectively reacting with substrates or inhibitors resembling the substrates in the structure thereof.

Addition of a ligand, i.e. substrate or an analogue thereof to an inert carrier provides a specific sorbent which is capable of selectively combining, from a complex mixture of compounds, an enzyme only. After washing the sorbent with a suitable solution for elimination of impurities, the enzyme retained by the sorbent is desorbed by means of a solution which is selected so as to dissociate the enzyme-ligand complex (variation of pH, elevation of the salt concentration, addition of organic solvents). The resulting enzyme product is generally enriched, to a substantial degree, with the desired enzyme and frequently it comprises a pure enzyme. The method makes it possible to substantially increase yields of enzymes and considerably improve quality of purification thereof.

Also known in the art are methods for purification and isolation of proteolytic enzymes which are based on ion exchange chromatography. Special mention should be made of the method based on chromatography on modified silochromes. However, this method is insufficiently selective, and is unsuitable for certain technical applications such as recovery of enzymes at a high yield directly from a fermentation broth or gastric juice, i.e. from mixtures with a low concentration of an active enzyme containing a large amount of inorganic and organic impurities including colored ones.

Further known in the art is a method for recovery and purification of neutral and alkaline proteinases from a brewing wort by means of a phenol-formaldehyde sulphocationite Duolite 10. The purification process involves 6 successive stages in addition to dialysis and lyophilization, i.e. double precipitation of the protein fraction with acetone, followed by centrifugation, double chromatography on a DEAE-cellulose, purification on Duolite 10 and precipitation by means of ammonium sulphate.

Duolite 10 in this case is used for the removal of colored impurities from the mixture, not for a direct separation of individual enzymes. The final object of using it is separation of a mixture of neutral and alkaline proteinases with a yield ranging from 33 to 67%.

In this method for recovering enzymes, biospecific sorbents are most extensively used which are prepared from agarose activated by bromocyane and covalently bonded with compounds specific for this particular class of enzymes, i.e. ligands.

In the prior art methods for purification of enzymes use is made of biospecific sorbents prepared by interaction of Sepharose 4B activated with cyanogen bromide with such peptide ligands as methyl ether and amide of $\epsilon$-aminocapronyl-D-phenylalanine, methyl ether of $\epsilon$-aminocapronyl-L-phenylalanine-D-phenylalanine; N-2,4-dinitrophenylhexamethylene diamine and an antibiotic, i.e. Gramicidin S. This method, however, has certain disadvantages. The main disadvantage resides in that the above-mentioned ligands (except Gramicidin S) can be obtained only by an extensive multi-stages synthesis, whereby the preparation of sorbents is hampered.

Also known in the art is a method for purification of enzymes with the use, as biospecific sorbents, of Sepharose 4B covalently bonded with an antibiotic Gramicidin S (cf. "Biokhimija" (Biochemistry), vol. 41, 2, 294; 1976).

A sorbent containing, as a ligand, a known antibiotic Gramicidin C, however, finds limited application prepared in a relatively simple manner. At present, Gramicidin C, however, finds but a limited application in medicine and is produced in small quantities. Disadvantages of a sorbent based on Gramicidin S-Sepharose 4B may be exemplified by difficulties encountered in the synthesis of the sorbent owing to a very low solubility of Gramicidin S. Reaction of Gramicidin S with Sepharose 4B activated with bromocyane is conducted in solutions with a high content of dimethylformamide which might partly destroy the structure of Sepharose. In the sorbent synthesis Gramicidin S settles, thus reducing the final product yield and hindering the product purification. Furthermore, the range of application of Gramicidin S-Sepharose 4B is limited to certain classes of proteinases and does not involve practically important serine proteinases.

It is an object of the present invention to overcome the above-mentioned disadvantages.

It is an object of the present invention to provide such a method which makes it possible to selectively recover and purify proteolytic enzymes from naturally-occurring sources.

It is another object of the present invention to provide a simplified method for purification of proteolytic enzymes.

SUMMARY OF THE INVENTION

These objects are accomplished by the purification of proteolytic enzymes is performed by way of a biospecific sorption of dissolved proteolytic enzymes on a sorbent, i.e. a derivative of agarose chemically combined with a ligand, followed by elution of the sorbed enzymes with salt buffers. In accordance with the present invention biospecific sorption of proteolytic enzymes is effected using a sorbent prepared by a covalent addition, to agarose, of a naturally-occurring polypeptide bacitracin.

The method according to the present invention is especially efficient for recovering enzymes directly from a fermentation broth containing colored impurities. A colorless enzyme is recovered by means of bacitracin-sepharose; in doing so, a substantial effect is obtained in a single-stage process of its purification owing to the sorbent selectivity. Moreover, the novel biospecific sorbent according to the present invention can be utilized for operation with solutions within a wide range of pH values (of from 1.8 to 8.0) wich enables its use for recovering proteolytic enzymes of different classes including carboxyl, thiol, serine, metalproteinsases and exopeptidases.

By using the novel biospecific sorbent according to the present invention, it is possible to recover, with a yield of from 74 to 95%, various proteolytic enzymes with an increase of activity of 2 to 500 times depending on purity of the starting compound.

The present invention makes it possible to enlarge the range of applications of the sorbent using a pH interval most suitable for the stability and activity of the enzyme being recovered; besides, there is no necessity in correction of pH of a biological liquid or an extract, wherefrom the enzyme is recovered. Thus, an individual enzyme subtilisine can be now recovered from a coloured culture liquid of Bacillus subtilis in a single stage with a product yield of 90%.

In accordance with the present invention it is advisable that the biospecific sorption be effected using a solution of carboxyl proteinases with a pH value within the range of from 1.8 to 5.6 or from a solution of serine proteinases with a pH within the range of from 6 to 7.5.

In certain cases it is desirable to wash the sorbent with concentrated solutions of salts to remove non-specific sorbed proteins; thus in the purification of pig and horse peps in it is advisable to wash to sorbent with a 1M solution of sodium chloride in an acetate buffer at a pH of 5.0.

Other objects and advantages of the present invention will now become more fully apparent from the following detailed disclosure of the method for purification of proteolytic enzymes and examples illustrating the same.

DETAILED DISCLOSURE

The method according to the present invention makes it possible to recover and purify proteolytic enzymes from partially purified commercial preparations of enzymes, commercial complex preparations of process enzymes, biological liquids, extracts of organs and tissues, cells and cultural liquids of microorganisms.

The method according to the present invention is based on a biospecific sorption of dissolved proteolytic enzymes on a sorbent, viz. a derivative of agarose chemically, e.g. covalently, combined with a ligand. It is advisable to use, as the ligand in accordance with the present invention, an antiobiotic bacitracin comprising a naturally-occurring cyclododecapeptide containing three D-aminoacids. It is a non-competing inhibitor of the proteinase series.

It is likely that this is responsible for a specific interaction of the novel sorbent with proteolytic enzymes of different classes. Bacitracin is readily soluble in water. A great number of reactive groups in a molecule thereof makes it possible to perform the synthesis of the sorbent under mild conditions with varius kinds of activated sepharose, At the present time bacitracin is an inexpensive and readily available antibiotic, since it is produced on a commercial scale for animal husbandry.

As a carrier use is made of an inorganic polymer having free hydroxyl groups suchas agarose or derivatives thereof, e.g. different types of sepharose such as sepharose 4B, sepharose 6B, ultra-gel. The carrier material is insoluble under the conditions of use thereof.

The sorbent employed in the method according to the present invention can be obtained by a conventional process as follows.

Sepharose is treated with cyanogen bromide, whereafter the activated sepharose reacts with bacitracin at the δ-amino group of ornithine according to the following scheme:

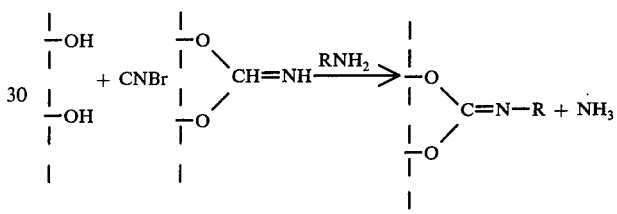

wherein R–NH$_2$ is the antibiotic bacitracin.

Purification of proteolytic enzymes is performed in the following manner.

Generally, a solution of a non-purified enzyme is brought into contact with the biospecific sorbent, i.e. bacitracin-sepharose 4B using dynamic or static sorption conditions. In doing so, selective bonding of proteinases with an insoluble carrier occurs. Then the sorbent with the combined protein is washed with a respective salt buffer such as glycin, phosphate, borate, acetate, tris. HCl, cytrate buffer. This results in separation of impurities, i.e. proteins, enzymes of other nature, low-molecular contaminants, pigments.

As the eluents use is made of salt solutions of different concentrations such as sodium chloride, potassium chloride, lithium chloride, ammonium sulphate. In the cases where the enzyme is bonded to the sorbent so strongly that it cannot be eluted by means of salt solutions, the latter are added with organic solvents contributing to a more effective desorption such as propanol, ethanol, sec. butanol, acetic acid and propionic acid.

The purified enzyme is used in the form of a solution or lyophilically dried after desalting by means of gel-filtration or dialysis.

The method according to the present invention is applicable for operaton with solvents within a wide range of pH values (of from 1.8 to 8.0) which makes possible to employ it for recovering, proteolytic enzymes of different classes including carboxyl, serine, thiol, metalproteinases, exopeptidases. Owing to the method of the present invention, it is possible to purify, with a yield of from 75 to 95%, various proteolytic enzymes with an increase in activity by 2 to 500 times depending on the purity grade of the starting compound.

EXAMPLE 1

Preparation of bacitracin-Sepharose 4B

For the synthesis use has been made of BrCN-activated Sepharose 4B (available from "Pharmacia", a Swedish company) and antibiotic bacitracin (Serva). To 1 g of a dry BrCN-activated sepharose 4B, distilled water is added for swelling, then the product is washed on a glass filter with 200 ml of $10^{-3}$M HCl over 15 minutes to remove sodium azide. The Sepharose 4B is washed with water to a negative reaction for Cl- and placed into a solution of 0.1 M with respect to NaHCO$_3$ and 0.5M with respect to NaCl; pH is 10. To the thus-prepared BrCN-activated Sepharose 4B there is added a solution of 100 mg of bacitractin in 5 ml to a solution of 0.1 M with respect to NaHCO$_3$ and 0.5M with respect to NaCl; pH = 10. The reaction is conducted at room temperature while maintaining the reaction mixture pH within the range of from 9.5 to 10.5.After 3 hours the gel is filtered-off and washed with a solution of 0.1 M with respect to NaHCO$_3$ and 0.5M with respect to NaCl; pH = 10. Thereafter it is washed with 0.1M NaHCO$_3$ and distilled water. The content of bacitracin is 2μmol/ml of the wet sorbent.

EXAMPLE 2

Purification of avamorin-carboxyl proteinase of *Aspergillus awamori* on bacitracin-Sepharose 4B A 0.1M acetate buffer solution with pH = 5.0 containing non-purified proteinase with a specific activity of 3.9 units/mg is passed through a chromatographic column filled with bacitracin-Sepharose 4B. Then the sorbent is washed with the starting buffer; active enzyme is eluted with a 1M NaCl solution in the same buffer. Specific activity of avamorin in the eluate is 30 units/mg; the yield relative to activity is 70-80%.

EXAMPLE 3

Purification of horse pepsin on bacitracin-Sepharose

Gastric juice of a horse having a pH of 1.8 or a solution of non-purified horse peptase with a specific activity of 6.3 units/mg in a 0.1M acetate buffer with a pH of from 2 to 5.6 (preferably 5.0) is passed through a chromatographic column filled with bactracin-Sepharose. Then the sorbent is successively washed with the starting buffer, a 1M NaCl solution in the same buffer and a 25% isopropanol in 1 M NaCl; pH 5.0. The isopropanolic fraction of the eluate containing the active protein is collected. Specific activity of peptase as determined by the Anson method is 46 activity units/optic unit. After desalting on a Sephadex G-25, the solution is lyophilized to give an enzyme with a specific acitivity of 60 units/mg. The yield relative to activity is 70-80%.

EXAMPLE 4

Purification of subtilisine on bacitracin-Sepharose

A fermentation broth of Bacillus subtilis A-50 with a pH value of about 8.0 and specific activity of 0.018 activity units/optic unit with respect to a synthetic substrate, i.e. p-nitroanilide of carbobenzoxy-L-alanyl-L-alanyl-L-leucin is intermixed for 30 minutes with bactracin-Sepharose and then the sorbent is carefully filtered-off using a glass filter and washed with a 0.1M phosphate buffer with a pH value of from 6.0 to 8.0 (preferably from 6.0 to 6.5), 1 M NaCl in the same buffer. Colored and other impurities are thus separated. The washed sorbent is placed into a chromatographic column. The active enzyme is eluted with a 25% propanol in a 1M NaCl, pH = 7.0 to give subtilisine with a specific activity of 2.5 units/mg. The yield with respect to activity is 86%.

EXAMPLE 5

Purification of fungous proteinase of *Aspergillus foctidus* on bacitracin-Sepharose 4B A 0.1 M acetate buffer solution having a pH=4.5 containing preliminarily purified (by means of ion-exchange chromatography) proteinase with a specific activity of 7 units/optic unit is passed through a chromatographic column filled with bacitracin-Sepharose 4B. Then the sorbent is washed with the starting buffer; the active enzyme is eluted with a 15% isopropanol in a 1M NaCl solution having a pH of 4.5. Specific activity of the proteinase in the eluate is 21.2 activity units/optic unit; the yield with respect to activity is 96%.

EXAMPLE 6

Purification of commercial preparation of pig pepsin on bacitracin-Sepharose.

A preparation of pig pepsin with a specific activity of 19 units/mg is intermixed with 0.1 M acetate buffer with the pH = 5.0; the insoluble precipitate is filtered-off. The filtrate is placed into a column with bacitracin-Sepharose. Then the sorgent is washed with the same buffer, 1 M NaCl, 25% isopropanol in 1M NaCl with the pH = 5.0. The isopropanol fraction of the eluate containing the active protein is collected. Specific activity of the enzyme is increased, as compared to the starting activity, by 2.5 times; the yield relative to activity is 98%.

EXAMPLE 7

Purification of commercial preparation of alkaline proteinase of Bacillus subtilis (subtilopeptidase A)

A 0.1 M phosphate buffer having a pH=8.0 containing an alkaline proteinase of *Bacillus subtilis* with the specific activity of 3.0 units/mg relative to p-nitroanilide of carbobenzoxy-L-alanyl-L-alanyl-L-leucin is passed through a column filled with bacitracin-Sepharose. The sorbent is washed with the same buffer, the active enzyme is eluted with a 25% isopropanol in 1M NaCl having a pH=8.0. Subtilisine is obtained with a specific activity of 4.0 units/mg. The yield relative to activity is 75%.

What is claimed is:

1. A method for purification of proteolytic enzymes comprising a biospecific sorption of dissolved proteolytic enzymes on a sorbent prepared by a chemical addition of the naturally-occurring polypeptide bacitracin, to agarose activated with cyanogen bromide; elution of the sorbed proteolytic enzymes with salt buffers.

2. A method for purification of proteolytic enzymes according to claim 1, wherein said biospecific sorption is performed from a solution of carboxyl proteinases with a pH of from 1.8 to 5.6.

3. A method for purification of proteolytic enzymes according to claim 1, wherein said biospecific sorption is performed from a solution of serine proteinases with a pH of from 6 to 7.5.

* * * * *